Figure 1:
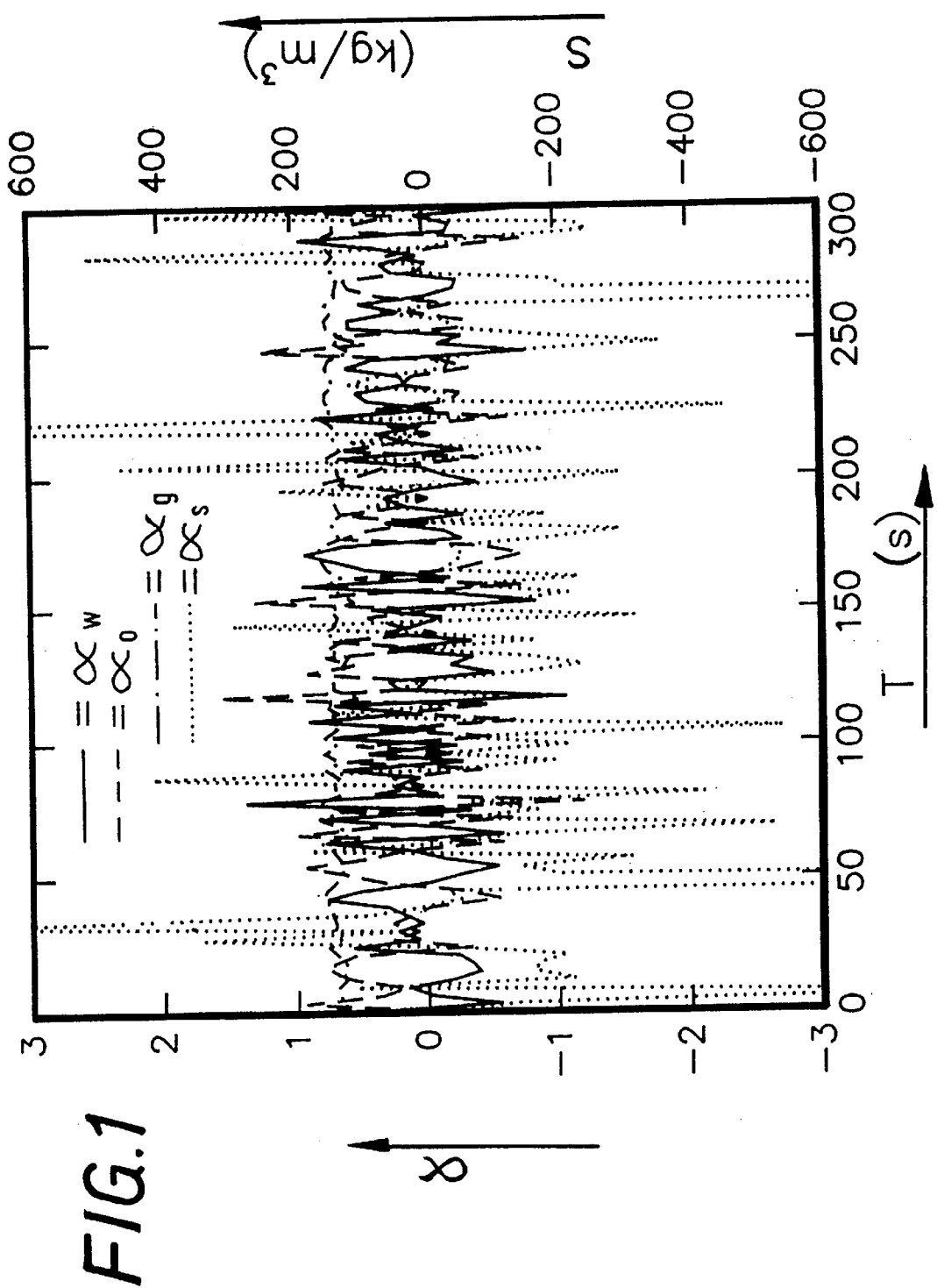

United States Patent [19]

Slijkerman et al.

[11] Patent Number: 5,854,820

[45] Date of Patent: Dec. 29, 1998

[54] METHOD AND METER FOR MEASURING THE COMPOSITION OF A MULTIPHASE FLUID

[76] Inventors: Walter Fredericus Johannes Slijkerman; Alexander Meijnhart Scheers, both of Volmerlaan 6, 2288 GD Rijswijk, Netherlands

[21] Appl. No.: 63,083

[22] Filed: Apr. 21, 1998

Related U.S. Application Data

[63] Continuation of Ser. No. 726,499, Oct. 7, 1996.

[30] Foreign Application Priority Data

May 2, 1996 [EP] European Pat. Off. ............... 96201214

[51] Int. Cl.[6] ..................................................... G01N 23/06
[52] U.S. Cl. ................................................ 378/51; 378/53
[58] Field of Search ................................. 378/51, 53, 57; 250/356.1

[56] References Cited

U.S. PATENT DOCUMENTS

| | | | |
|---|---|---|---|
| 4,200,789 | 4/1980 | Arnold et al. | 250/270 |
| 4,352,288 | 10/1982 | Paap et al. | 73/61 |
| 4,365,154 | 12/1982 | Arnold et al. | 250/270 |
| 4,618,975 | 10/1986 | Glantschnig | 378/51 |
| 5,654,551 | 8/1997 | Watt et al. | 250/356.1 |

FOREIGN PATENT DOCUMENTS

| | | |
|---|---|---|
| 0236623 A1 | 9/1987 | European Pat. Off. . |
| 2083908 | 9/1980 | United Kingdom . |
| 2088050 | 10/1980 | United Kingdom . |
| 94/25859 | 11/1994 | WIPO . |

OTHER PUBLICATIONS

International Search Report dated 27 Aug. 1997.

*Primary Examiner*—David P. Porta
*Assistant Examiner*—David Vernon Bruce

[57] ABSTRACT

The composition of a multiphase fluid with varying salinity is measured by radiating a photon beam through the fluid and measuring the level of radiation absorption by the fluid at at least radiation energy levels and feeding the thus obtained radiation absorption data to a data processor which generates data concerning the fluid composition, including its salt content, if any, on the basis of a phase fraction calculation scheme in which radiation absorption by salt is taken into account.

7 Claims, 2 Drawing Sheets

METHOD AND METER FOR MEASURING THE COMPOSITION OF A MULTIPHASE FLUID

This is a continuation of application Ser. No. 08/726,499 filed Oct. 7, 1996, the entire disclosure of which is hereby incorporated by reference.

The invention relates to a method and meter for measuring the composition of a multiphase fluid by transmitting a photon beam therethrough.

More particularly, the invention relates to a method and meter for measuring the composition of the multiphase fluid mixture produced by one or more crude oil production wells where the crude oil is usually accompanied by varying quantities of natural gas and/or water. Such a measurement provides information on the fluid composition and flow pattern in the pipeline from each well which generates insight needed for an optimal control of the production system and the producing crude oil reservoir.

Several techniques exist for measuring the composition of such a multiphase fluid by radiating a photon beam therethrough, where the photon beam is usually generated by a gamma- and/or X-ray source.

These techniques take into account that the absorption of photon beam radiation in any material can be expressed by the formula: $\ln I_o/I = \mu \rho d$, where:

$I_o$ is the intensity of the generated radiation;
I is the intensity of the transmitted radiation;
$\mu$ is the radiation mass absorption coefficient of the material;
$\rho$ is the density of the material; and
d is the transmission length of the radiation through the material.

These techniques also take into account that at a specific radiation energy level each material has a specific radiation mass absorption coefficient $\mu$ which is typical for that material and moreover that when the radiation level is varied also the radiation mass absorption coefficient $\mu$ will vary in a way which is typical for that material.

International patent application PCT/EP 94/01320 discloses a method for measuring the composition of a multiphase fluid produced by an oil well by transmitting a photon beam therethrough and detecting the level of radiation absorption at two radiation energy levels. The known method also takes into account that the sum of the three fractions oil, water and gas broadly equals to one, i.e. makes up about 100% of the fluid flowing through the pipeline, so that a set of three mathematical equations can be set up whereby the measured data are processed to generate information on the fluid composition.

European patent specification No. 236623 discloses that it may be useful to detect the level of photon beam radiation absorption at more than two energy levels in order to generate a more extensive data set of radiation absorption data from which the fluid composition can be deduced. This known method also includes the opportunity to take into account radiation absorption caused by sand particles entrained in the fluid mixture and the sulphur content of the crude oil produced by using additional radiation systems which radiate photon beams at still other energy levels.

Although these known composition metering techniques provide useful information it has been found that the known meters require extensive calibration which is to be regularly updated, but that nevertheless some inaccuracy in the measurements still remained.

It is an object of the present invention to enhance the accuracy of multiphase fluid composition measurement techniques and to allow simpler and less frequent calibration procedures for multiphase composition meters.

The method according to the invention thereto comprises measuring the composition of a multiphase fluid by radiating a photon beam therethrough and measuring the level of radiation absorption by the fluid at at least three radiation energy levels; and feeding the measured radiation absorption data to a data processing unit which is programmed such that it performs calculations in accordance with a phase fraction calculation scheme on the basis of said radiation absorption data and that it generates data concerning fluid composition, including its salt content, if any, on the basis of said calculations.

The method according to the invention is based on the insight that the salt content, if any, of the water produced by e.g. a crude oil production well may have a significant impact on the photon beam radiation absorption by the fluid.

In a preferred embodiment, the method according to the invention comprises:

measuring the level of radiation absorption by the fluid by measuring the transmitted radiation count rate at three radiation energy levels, wherein the logarithms of the measured count rates at said three energy levels are expressed as $I_1$, $I_2$ and $I_3$ and the calculation scheme comprises the following matrix equation scheme:

$$\begin{bmatrix} I_1 \\ I_2 \\ I_3 \\ 1 \end{bmatrix} = \begin{bmatrix} \mu_{w1}\rho_w|_{ini} & \mu_{o1}\rho_o & \mu_{g1}\rho_g & \mu_{s1} + (R-1)\mu_{h_2o1} \\ \mu_{w2}\rho_w|_{ini} & \mu_{o2}\rho_o & \mu_{g2}\rho_g & \mu_{s2} + (R-1)\mu_{h_2o2} \\ \mu_{w3}\rho_w|_{ini} & \mu_{o3}\rho_o & \mu_{g3}\rho_g & \mu_{s3} + (R-1)\mu_{h_2o3} \\ 1 & 1 & 1 & 0 \end{bmatrix} \begin{bmatrix} \alpha_w \\ \alpha_o \\ \alpha_g \\ \Delta S \alpha_w \end{bmatrix}$$

where:
$\rho$ refers to the density of a fluid fraction in kg/m³
$\mu$ refers to the mass absorption coefficient in m²/kg
$\alpha$ refers to the mass fraction of a component in the fluid
R refers to the rate of water density increase per unit increase of salinity
$\Delta S$ refers to change in salinity in kg/m³
the subscript w refers to saline water
the subscript s refers to salt
the subscript o refers to crude oil
the subscript h₂o refers to fresh water and
the subscript ini refers to an initial state; and
the data processing unit is programmed to solve said matrix equation scheme.

It will be understood by those skilled in the art that the parameters in the above matrix equation scheme may be identified by symbols that differ from those used above and that the scheme may be set up in a different manner. The equation scheme can be solved in several ways, which have in common that they can be identified as matrix inversion techniques. However, irrespective of these variations and deviations it is essential in accordance with the present invention that in any calculation scheme radiation absorption by the salt content of the fluid is taken into account.

Computer simulations in which the above calculation scheme is used demonstrate, however, that the thus measured salinity and phase fractions, in particular the measured water content of the fluid, become sensitive to statistical fluctuations in the measured count rates.

To suppress this sensitivity it is preferred that the level of radiation absorption is measured repeatedly and the data processing unit is programmed such that it takes into account that the salt content of an aqueous fraction of the fluid remains substantially constant over a time interval which is limited to less than several hours and such that it solves said matrix equation scheme by finding a statistical optimum.

The assumption that the salinity of the produced water is substantially constant on a time scale of a few hours. prevents the matrix equation scheme from being solved exactly. A suitable method for finding a solution for the equation scheme is to find a statistically optimal solution in a chi-square minimization sense on the basis of a function minimization technique. This technique is described in the handbook "Computational methods in optimization", written by E. Polak and published by Academic Press, New York in 1971.

If photon beam absorption is measured at three energy radiation levels a few hours of radiation absorption data are needed to determine the statistically optimal value of salinity with sufficient statistical certainty. The minimum acquisition time can be reduced by using more than three energy levels.

The meter according to the invention comprises a source for radiating a photon beam through the fluid, a radiation detector for measuring the level of radiation absorption by the fluid at at least three radiation energy levels, and a data processing unit which is programmed such that it performs calculations in accordance with a phase fraction calculation scheme on the basis of the radiation absorption data and that it provides data concerning fluid composition, including its salt content, if any, on the basis of said calculations.

These and other features, objects and advantages of the method and meter according to the invention will become apparent from the following detailed description, claims, drawings and abstract.

Figure 2:
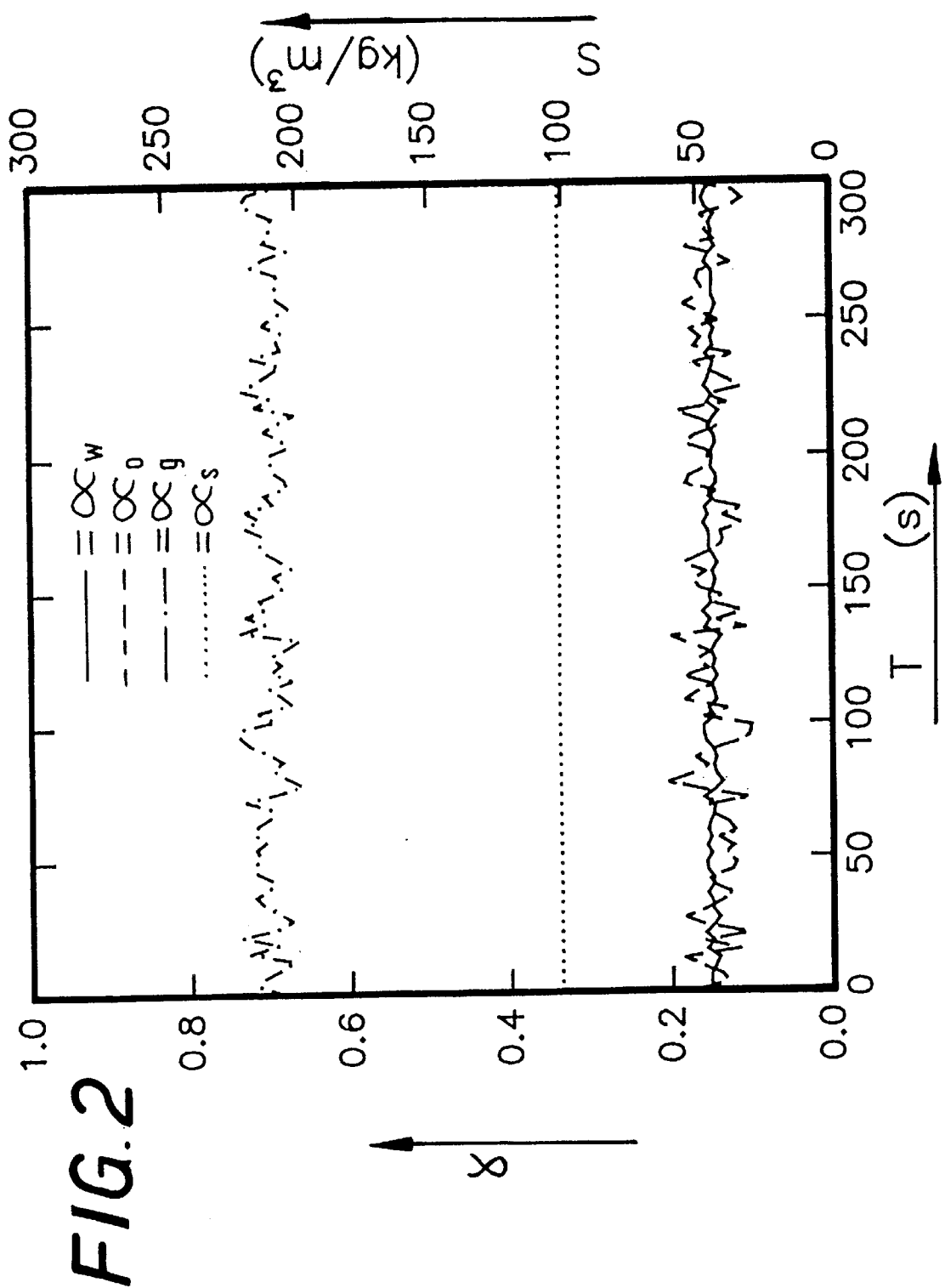

The invention will now be described by way of example with reference to the accompanying drawings in which:

FIG. 1 is a diagram showing a graphical representation of the results of directly solving the matrix equation scheme according to the invention for the conditions outlined below; and FIG. 2 is a diagram showing a graphical representation of the results of using a chi-square minimization algorithm to solve the matrix equation scheme according to the invention.

In FIGS. 1 and 2 the left hand scale is valid for the phase fraction $\alpha$ of water w, oil o, gas g and salt s and the right hand scale salinity S in kg/m$^3$. The horizontal scale is a timescale where the time t is expressed in seconds (s).

Field experience has indicated that variations in salinity occur in wells producing from water injected reservoirs and that the produced water may be a mixture of formation water and injection water each with its own salinity.

A full ion analysis of water produced by various wells producing from a water injected crude oil reservoir demonstrated that the salinity is different per well. The wells produced water with a salinity between that of formation water (160 kg/m$^3$) and injection water (35 kg/m$^3$).

Furthermore, in a six month period the salinity for some wells had changed with more than 10 kg/m$^3$.

The high-resolution solid-state detection technology described in International patent application PCT/EP 94/01320 allows the 13.9, 17.8, 22, 26.3 and 59.5 keV energy levels of a photon beam radiated by an Am-241 gamma ray source to be resolved and hence these levels are available for salinity determination.

Salts are dissolved in the produced water and as such they do not represent a volume fraction. The linear absorption coefficient in saline water is the sum of the linear absorption coefficients in salt and fresh water:

$$\rho_w \mu_w = \mu_s S + (\rho_w - S)\mu_{h_2o}$$

where salinity S represents the amount of salt (in kg) present in a m$^3$ of saline water and $\mu_w$, $m_s$ and $\mu_{h_2o}$ are the mass absorption coefficients of the saline water, salt and fresh water, respectively.

Saline water density $\rho_w$ approximately increases linearly with salinity. The rate of increase is different for every salt and is in the range 0.6–0.9.

Saline water density is hence described by:

$$\rho_w = \rho_{h_2o} + RS$$

where R refers to the water density increase per unit increase of salinity S.

Combination of these equations yields:

$$\rho_w \mu_w = \rho_{h_2o}\mu_{h_2o} + (\mu_s + [R-1]\mu_{h_2o})S$$

In case the meter is calibrated at initial salinity $S_{ini}$ and $\Delta S$ represents the salinity change, the following equation is obtained $$\rho_w \mu_w = \rho_w \mu_w|_{ini} + (\mu_s + [R-1]\mu_{h_2o})\Delta S$$

By measuring radiation absorption at three energy levels 1, 2 and 3, respectively and taking into account that in a crude oil production well the sum of the oil, gas and aqueous fractions are substantially equal to one, the following matrix equation scheme can be set up:

$$\begin{bmatrix} I_1 \\ I_2 \\ I_3 \\ 1 \end{bmatrix} = \begin{bmatrix} \mu_{w1}\rho_w|_{ini} & \mu_{o1}\rho_o & \mu_{g1}\rho_g & \mu_{s1}+(R-1)\mu_{h_2o1} \\ \mu_{w2}\rho_w|_{ini} & \mu_{o2}\rho_o & \mu_{g2}\rho_g & \mu_{s2}+(R-1)\mu_{h_2o2} \\ \mu_{w3}\rho_w|_{ini} & \mu_{o3}\rho_o & \mu_{g3}\rho_g & \mu_{s3}+(R-1)\mu_{h_2o3} \\ 1 & 1 & 1 & 0 \end{bmatrix} \begin{bmatrix} \alpha_w \\ \alpha_o \\ \alpha_g \\ \Delta S \alpha_w \end{bmatrix}$$

or $$\vec{I}_m = M\vec{\alpha}$$

This is a solvable system of equations. From a measurement of the transmitted gamma-ray absorption at the three levels the phase fractions and salinity change $\Delta S$ are found by solving this matrix equation scheme. It can be shown that the inverse of matrix M is poorly conditioned such that statistical measurement errors in $\vec{I}_m$ may lead to large errors in the measured phase fractions and salinity. To evaluate the feasibility of the composition measurement using three or more energy levels the whole measurement process was simulated in the computer simulation described below.

In the computer simulation a base case situation as defined in the following Table was used:

| Oil density | $\rho_o =$ | 800 | kg/m$^3$ |
|---|---|---|---|
| Gas density | $\rho_g =$ | 30 | kg/m$^3$ |
| Saline water density | $\rho_w =$ | 1070 | kg/m$^3$ |
| Water salinity | $S =$ | 100 | kg/m$^3$ |
| Salt composition | | NaCl | |
| Absorption path length | | 0.05 | m |

The simulation consisted of the following six steps:

Step 1

Calculate the linear absorption coefficients for oil, saline water and gas. These are calculated from the base case parameters as defined above. From these parameters the linear absorption coefficients for water, oil, gas and salt are computed from tabulated atomic absorption coefficients.

Step 2

Choose a combination of water, oil and gas fractions $\vec{\alpha}$, initial salinity $S_{ini}$ and change in salinity $\Delta S$.

Step 3

The expected count rates are calculated using the matrix equation scheme. The empty pipe count rates for the three energy levels are needed. These were chosen realistically according to field trials and are tabulated below.

| Energy level (keV) | Count rate (s$^{-1}$) |
|---|---|
| 17.8 | 21000 |
| 26.3 | 2000 |
| 59.5 | 80000 |

Step 4

The counting process is subjected to statistical fluctuations. The measured count rates will vary around the calculated count rates according to a Poisson distribution. In the computer simulation measured count rates are generated by drawing them randomly from a Poisson distribution with a mean and variance given by the calculated count rate. Typically, 3600 sets of 3 measured count rates, each simulating a 3 second measurement interval, were simulated.

Step 5

These simulated count rates were then converted to water, oil and gas fractions $\alpha_w$, $\alpha_o$, $\alpha_g$ and salinities S by solving the matrix equation scheme according to the invention.

A graphical representation of the results of this procedure is shown in FIG. 1. Input phase fractions in this case are steady in time with water fraction $\alpha_w=0.15$, oil fraction $\alpha_o=0.15$ and gas fraction $\alpha_g=0.70$. Input initial salinity $S_{ini}$ was chosen to be zero and a change in salinity $\Delta S$ of 100 kg/m$^3$ was taken. FIG. 1 shows large fluctuations in the water and oil fractions $\alpha_w$, $\alpha_o$ and salinity S. Gas fraction $\alpha_g$ is relatively insensitive to statistical fluctuations in count rates. It is concluded that the measured phase fractions (in particular watercut $\equiv \alpha_w/(\alpha_o+\alpha_w)$) and salinity become extremely sensitive to the statistical variations in the measured count rates. It follows that in this situation solving the equations for each measurement does not yield a practical composition measurement.

To improve the phase fraction computation a statistical chi-square minimization algorithm was devised that exploits the fact that salinity of the produced water is unlikely to fluctuate over a 3-second time interval. Field experience has taught that salinity changes either on timescales of months (gradual change from formation water to injected water) or on timescales of days (sudden injection water breakthrough) and that the time span of a few hours salinity does hardly change. This observation is used in the phase fraction computation to arrive at a better composition measurement. Phase fractions have to be found such that a constant salinity is obtained. Keeping salinity constant for all datasets implies that for every simulated 3-second measurement the matrix equation scheme according to the invention cannot be solved anymore, as the exact solution is the noisy result in FIG. 1. Instead a solution has to be found which is optimal in a chi-square minimisation sense. That solution then provides the individual phase fractions for all datasets and a single, constant value of salinity which is valid for all sets.

The chi-square $\chi^2$ to be minimised is defined as follows:

$$\chi^2_{total} = \frac{\sum_{n=1}^{n} \sum_{j=1}^{L} \left( \frac{I_{mji} - I_{cji}(\vec{\alpha_i})}{\sigma_{ji}} \right)^2}{n-1} = \frac{\sum_{i=1}^{n} \chi_i^2}{n-1}$$

in which n is the number of datasets, L is the number of energy levels available, where L is at least 3, and $I_{mij}$ and $I_{cij}$ are the logarithms of the measured resp. calculated count rates at level number j for dataset i. $I_{cij}$ is calculated from the phase fractions and salinity according to the matrix equation scheme, $\sigma_{ij}$ is the standard deviation in the determination of $I_{mij}$. (In the simulations $\sigma_{ij}$ is taken equal to the square root of $I_{mij}$ in accordance with Poisson statistics). The n sets of phase fractions and the single, constant value for salinity that minimises chi-square is the best solution to the measurement in a statistical sense.

Every dataset has 2 free parameters. Thus in total 2n+1 free parameters are available to minimise chi-square. According to the matrix equation scheme $I_{cij}$ is non-linear in its free parameters making the minimisation process a cumbersome exercise. The minimisation procedure is significantly simplified by separating the linear and non-linear part. For this particular minimisation problem such separation follows naturally from the definition of chi-square.

The following two step procedure is hence followed:

Step 1

The $I_{cij}$ are a function of $\Delta S$ and $\vec{\alpha_i}$ according to:

$$\begin{bmatrix} I_{c1} \\ I_{c2} \\ I_{c3} \end{bmatrix} =$$

$$\begin{bmatrix} \mu_{w1}\rho_w|_{ini} + \Delta S(\mu_{s1} + (R-1)\mu_{h_2o1}) & \mu_{o1}\rho_o & \mu_{g1}\rho_g \\ \mu_{w2}\rho_w|_{ini} + \Delta S(\mu_{s2} + (R-1)\mu_{h_2o2}) & \mu_{o2}\rho_o & \mu_{g2}\rho_g \\ \mu_{w3}\rho_w|_{ini} + \Delta S(\mu_{s3} + (R-1)\mu_{h_2o3}) & \mu_{o3}\rho_o & \mu_{g3}\rho_g \end{bmatrix} \begin{bmatrix} \alpha_w \\ \alpha_o \\ 1-\alpha_w-\alpha_o \end{bmatrix}$$

which follows from the matrix equation scheme and eliminating of $\alpha_g$. A trial salinity $\Delta S$ is chosen. For that $\Delta S$, $\vec{\alpha_i}$ is varied to arrive at a minimum $\chi_i^2$. As $I_c$ is linear in the phase fractions minimisation of $\chi_i^2$ can be performed using Singular Value Decomposition, which is a non-iterative technique and only involves matrix operations. In the minimisation process the phase fractions are constrained to the zero to one interval. Hence, a set of phase fractions within the zero to one interval are found that minimises $\chi_i^2$ for $\Delta S_{trial}$.

Subsequently, the total chi-square $\chi_{total}^2$ is computed by summing the n individual $\chi_i^2$ and subsequent normalisation.

Step 2

The total chi-square $\chi_{total}^2$ is a function of $\Delta S$ and will have a minimum for a certain $\Delta S$. The $\Delta S$ for which $\chi_{total}^2$ is minimal is the optimal solution. Locating that minimum is an iterative procedure for which, for example, a parabolic interpolation scheme can be used.

Using the above described phase fraction calculation scheme for the same set of simulated count rates as in FIG. 1 results in phase fractions and a salinity as shown in FIG. 2. FIG. 2 demonstrates that use of the statistical chi-square minimization algorithm results in a statistically acceptable phase fraction determination that is insensitive to changes in salinity.

In the chi-square minimisation algorithm there is no reason to limit the number of energy levels to three. In case more energy levels are available and the absorption at these levels can be measured they can be included in the phase fraction calculation scheme.

There is a clear advantage of incorporating as many as possible energy levels in the measurement process as the minimum required acquisition time decreases significantly. Incorporating the 22 keV level of an Am-241 gamma ray source in addition to the earlier mentioned 17.8, 26.3 and 59.5 keV levels reduces minimum acquisition time by a factor 3~4. Including the 13.9 keV level as the fifth level again yields a factor 7~8.

Another advantage of incorporating as many as possible energy levels is that the statistical accuracy of the composition measurement increases as, in total, more counts are used in the phase fraction determination. At low liquid loading the count rate obtained from the 17.8 keV level is dominant and not much statistical accuracy is gained by incorporating the 13.9, 22 and/or 26.3 keV levels. At high liquid loading the count rate in the 17.8 peak is comparable with those for the 22 and 26.3 keV levels.

The capability of the method according to the invention to detect a variation in salinity can also be used to simplify the calibration procedure of the composition meter. Instead of calibrating the meter with saline production water it can be calibrated with fresh water. The meter will measure a variation in salinity (away from the fresh water salinity) which is equal to the actual produced water salinity.

Further simplifications to the calibration procedure are possible. Fresh water absorption properties are known from tabulated data and thus the water reference count rate can in principle be computed on theoretical grounds from the count rates measured for an empty pipe. Consequently, calibration with water can be left out.

A similar line of arguments can be applied to oil reference count rate. Starting from the empty pipe count rates the reference oil and gas count rates can be calculated from the oil and gas densities and the carbon mass fraction of the oil and gas (for gas also the fraction of other gases such as $N_2$, $CO_2$, $H_2S$ needs to be known).

So, in the above described calibration procedure only a measurement of empty pipe count rates would suffice. This calibration work could typically be done by the manufacturer in the factory.

An advantage of the above-mentioned calibration procedure is that there is no need for on-line determination of reference count rates. This makes subsea application of this type of composition meter operationally simpler and more cost-effective. It also enables use of a flowmeter where the photon beam is transmitted through a large diameter pipe.

It will be understood by those skilled in the art that instead of the Am-241 radio-isotope photon flux source described hereinbefore other photon flux sources, such as an X-ray tube may be used as well.

An advantage of using an X-ray tube is that it can be switched off when the meter is not in use and that the photon output can be adjusted so that it increases in response to an increase of photon beam absorption by the fluid flowing through the meter.

It will further be understood by those skilled in the art that the matrix calculation scheme and chi-square minimization algorithm according to the invention can be incorporated into a data processor as a computing algorithm and that the data processor may generate a display which shows the oil, gas, water fractions and salinity of the produced multiphase fluid or a selection of these characteristics or derivatives thereof.

Finally, it will be understood that the method and meter according to the invention are useful for measuring the composition of any saline multiphase fluid in which radiation absorption by a saline fraction needs to be taken into account, provided that for fluids other than hydrocarbon well effluents the matrix calculation scheme and chi-square minimization algorithm are to be modified accordingly.

We claim:

1. A method for measuring the composition of a multiphase fluid by radiating a photon beam therethrough and measuring the level of radiation absorption by the fluid at at least three radiation energy levels; and feeding the measured radiation absorption data to a data processing unit which is programmed such that it performs calculations in accordance with a phase fraction calculation scheme on the basis of said radiation absorption data and that it generates data concerning fluid composition, including its salt content, if any, on the basis of said calculations, wherein the level of radiation absorption by the fluid is measured by measuring the transmitted radiation count rate at three radiation energy levels:

the logarithms of the measured count rates at said three energy levels are expressed as $I_1$, $I_2$ and $I_3$ and the calculation scheme comprises the following matrix equation scheme:

$$\begin{bmatrix} I_1 \\ I_2 \\ I_3 \end{bmatrix} = \begin{bmatrix} \mu_{w1}\rho_w|_{ini} & \mu_{o1}\rho_o & \mu_{g1}\rho_g & \mu_{s1}+(R-1)\mu_{h_2o1} \\ \mu_{w2}\rho_w|_{ini} & \mu_{o2}\rho_o & \mu_{g2}\rho_g & \mu_{s2}+(R-1)\mu_{h_2o2} \\ \mu_{w3}\rho_w|_{ini} & \mu_{o3}\rho_o & \mu_{g3}\rho_g & \mu_{s3}+(R-1)\mu_{h_2o3} \\ 1 & 1 & 1 & 0 \end{bmatrix} \begin{bmatrix} \alpha_w \\ \alpha_o \\ \alpha_g \\ \Delta S \alpha_w \end{bmatrix}$$

where:

$\rho$ refers to the density of a fluid fraction in $kg/m^3$ $\mu$ refers to the mass absorption coefficient in $m^2/kg$ $\alpha$ refers to the mass fraction of a component in the fluid R refers to the rate of water density increase per unit increase of salinity $\Delta S$ refers to change in salinity in $kg/m^3$ the subscript w refers to saline water the subscript s refers to salt the subscript o refers to crude oil the subscript $h_2o$ refers to fresh water and the subscript ini refers to an initial state; and the data processing unit is programmed to solve said matrix equation scheme.

2. The method of claim 1, wherein the level of radiation absorption is measured repeatedly and the data processing unit is programmed such that it takes into account that the salt content of an aqueous fraction of the fluid remains substantially constant over a time interval which is limited to less than several hours and such that it solves said matrix equation scheme by finding a statistical optimum.

3. The method of claim 2, wherein the data processing unit is programmed such that it finds said statistical optimum on the basis of a statistical chi-square minimization algorithm.

4. The method of claim 3, where the multiphase fluid is the effluent of a hydrocarbon fluid production well which produces crude oil together with natural gas and/or saline water and the phase fractions of said constituents fluctuate and may vary between 0% and 100% if the well produces said constituents in a slug flow regime.

5. A meter for measuring the composition of a multiphase fluid, comprising a source for radiating a photon beam through the fluid, a radiation detector measuring the level of radiation absorption by the fluid at at least three radiation energy levels, and a data processing unit which is programmed such that it performs calculations in accordance with a phase fraction calculation scheme on the basis of the radiation absorption data and that it provides data concerning fluid composition, including its salt content, if any, on the basis of said calculations; wherein the logarithms of the measured levels of radiation absorption at said three radiation energy levels are expressed as $I_1$, $I_2$ and $I_3$ and the calculation scheme comprises the following matrix equation scheme:

$$\begin{bmatrix} I_1 \\ I_2 \\ I_3 \end{bmatrix} = \begin{bmatrix} \mu_{w1}\rho_w|_{ini} & \mu_{o1}\rho_o & \mu_{g1}\rho_g & \mu_{s1} + (R-1)\mu_{h_2o1} \\ \mu_{w2}\rho_w|_{ini} & \mu_{o2}\rho_o & \mu_{g2}\rho_g & \mu_{s2} + (R-1)\mu_{h_2o2} \\ \mu_{w3}\rho_w|_{ini} & \mu_{o3}\rho_o & \mu_{g3}\rho_g & \mu_{s3} + (R-1)\mu_{h_2o3} \\ 1 & 1 & 1 & 0 \end{bmatrix} \begin{bmatrix} \alpha_w \\ \alpha_o \\ \alpha_g \\ \Delta S\alpha_w \end{bmatrix}$$

where:

$\rho$ refers to the density of a fluid fraction in kg/m$^3$ $\mu$ refers to the mass absorption coefficient in m$^2$/kg $\alpha$ refers to the mass fraction of a component in the fluid R refers to the rate of water density increase per unit increase of salinity $\Delta S$ refers to change in salinity in kq/m$^3$ the subscript w refers to saline water the subscript s refers to salt the subscript o refers to crude oil the subscript h$_2$o refers to fresh water and the subscript ini refers to an initial state.

6. The meter of claim 5, wherein the photon beam radiation source comprises a gamma-ray source.

7. The meter of claim 5, wherein the photon beam radiation source comprises an X-ray tube.

* * * * *